US00PP37311P2

(12) United States Plant Patent
Hansen

(10) Patent No.: US PP37,311 P2
(45) Date of Patent: Mar. 10, 2026

(54) ***DELOSPERMA* PLANT NAMED 'Electric Slide'**

(50) Latin Name: ***Delosperma* hybrid**
Varietal Denomination: Electric Slide

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,858

(22) Filed: Oct. 14, 2025

(51) Int. Cl.
*A01H 6/00* (2018.01)
*A01H 5/02* (2018.01)

(52) U.S. Cl.
USPC ..... Plt./422

(58) Field of Classification Search
USPC ..... Plt./263.1, 422
See application file for complete search history.

(56) References Cited

U.S. PATENT DOCUMENTS

PP36,547 P2 * 3/2025 Hansen ..... Plt./422

* cited by examiner

*Primary Examiner* — Karen M Redden

(57) ABSTRACT

A new and distinct cultivar of *Delosperma* plant named 'Electric Slide' is disclosed, characterized by abundant strong reddish-purplish petals nearly covering the plant. Plants have a low, mounding habit, and are tolerant to at least USDA zone 6. The new plant is useful for its. bright flowers and low habit in the landscape or as a container plant.

1 Drawing Sheet

Latin name of the genus and species: *Delosperma* hybrid. Variety denomination: 'Electric Slide'.

STATEMENT REGARDING PRIOR DISCLOSURES UNDER 37 CFR 1.77(B)(6)

*Delosperma* 'Electric Slide' was first sold or offered for sale by Walters Gardens, Inc. to North Coast Perennials on Oct. 15, 2024. The new plant was also listed on a website hosted by Walters Gardens, Inc. starting on Feb. 1, 2025, and in their "Walters Gardens 2025 2026 Catalog" first distributed on Jun. 3, 2025. No plants of *Delosperma* 'Electric Slide' have been sold in this country or anywhere in the world nor has any disclosure of the new plant been made more than one year prior to the filing date of this application, and such sale or disclosure within one year was either derived directly or indirectly from the inventor.

BACKGROUND OF THE INVENTION

The present invention relates to the new and distinct *Delosperma* cultivar named 'Electric Slide' also referred to here as the new plant. 'Electric Slide' was hybridized under direction of the inventor at a wholesale perennial nursery in Zeeland, Michigan, USA as the result of a greenhouse cross between 'PJS01S' (not patented) as the female parent and 'John Proffitt' (not patented) as the male parent in the summer of 2019. Seeds from this pollination were collected in the fall of 2019 and were sown earlier the next year. The new plant originated from a single seedling, was initially evaluated in the summer of 2021, selected for further evaluation, and assigned the breeder code 19-5-2.

*Delosperma* 'Electric Slide' has been successfully asexually propagated by shoot tip cuttings since 2021 at a wholesale perennial nursery in Zeeland, Michigan and found to produce identical stable and identical plants in successive generations of asexual propagation.

SUMMARY OF THE INVENTION

*Delosperma* 'Electric Slide' differs from the parents as well as all other Hardy Ice Plant cultivars known to the inventor. The most similar known *Delosperma* cultivars include: 'FSDD2117' U.S. Plant Pat. No. 36,476, 'Orchid Flash' U.S. Plant patent application Ser. No. 18/445,962, 'T1854' U.S. Plant Pat. No. 34,730, and 'Violet Wonder' (not patented).

'FSDD2117' has reddish-purple foliage and smaller flowers with petals that are more reddish and less purple. 'Orchid Flash' has larger flowers with longer petals that are lighter reddish-purple. 'T1854' has larger flowers with more petals with a lighter purplish-red color. 'Violet Wonder' has flowers with a lighter lilac in the outer petal portion and white on the inside.

The female parent, 'PJS01S', has flower petals that are fuchsia to reddish raspberry. 'John Proffitt' has petals that are lighter purplish-red with a white base.

*Delosperma* 'Electric Slide' differs from the above cultivars and all other cultivars of Hardy Ice Plant known to the inventor with the following repeatable distinguishing characteristics in combination:

1. Flowers with strong reddish-purple petals;
2. Low, mounded habit with good flower coverage, flowering on shoot tips and nodes;
3. Moderately evergreen, winter hardy to at least USDA Zone 6, and with good drought and heat tolerance.

BRIEF DESCRIPTION OF THE DRAWINGS

The photographs of the new plant demonstrate the overall appearance of the new plant, including the unique traits. The colors are as accurate as reasonably possible with color reproductions. Ambient light spectrum, source, and direction may cause the appearance of minor variations in color.

DETAILED BOTANICAL DESCRIPTION

Figure 1:
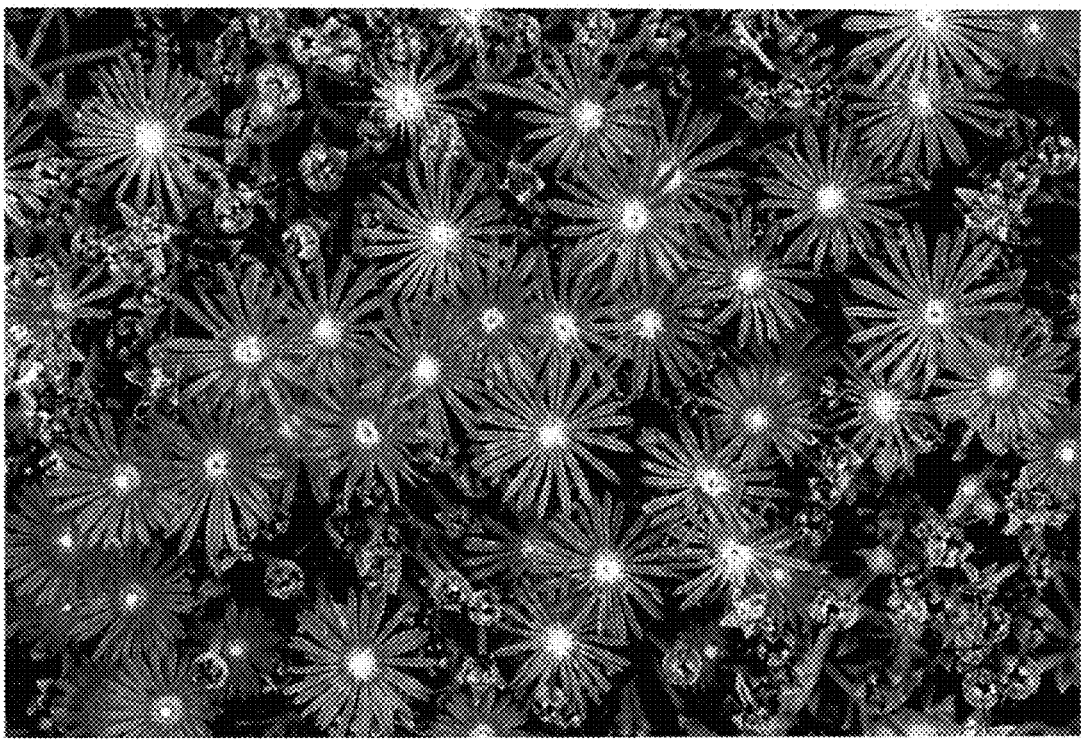
FIG. 1 shows the top-view habit of a two-year-old plant in early flowering.
Figure 2:
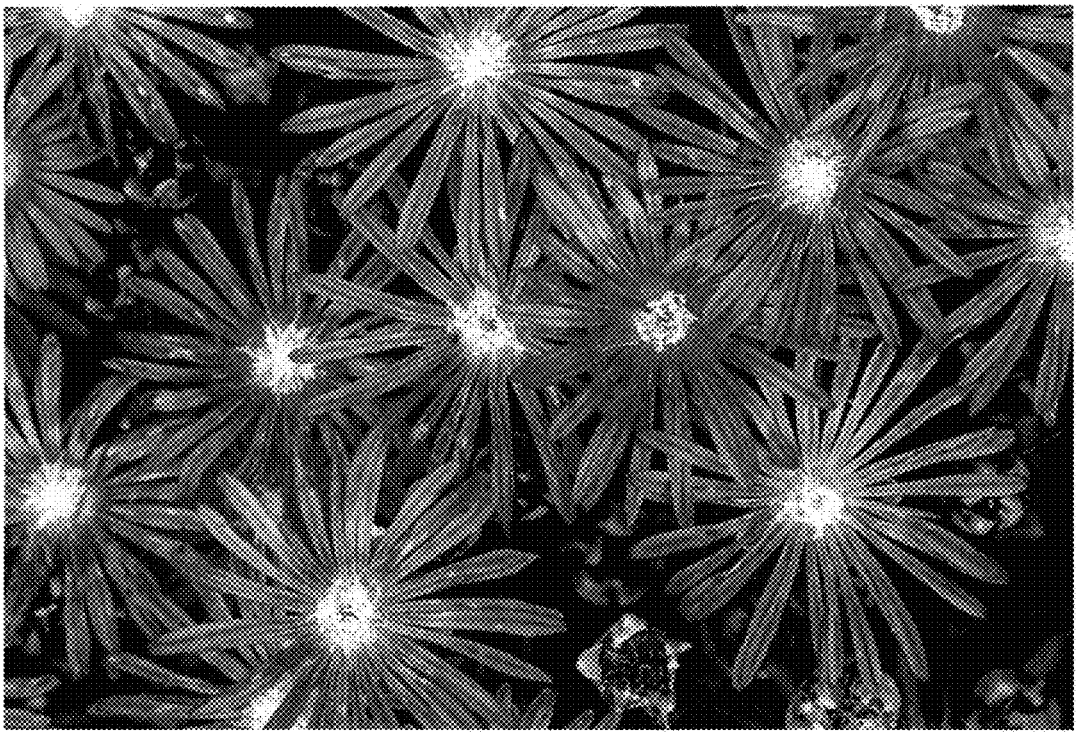
FIG. 2 shows a close-up of the flowers and young buds of a two-year-old plant.

The following is a detailed description of two-year-old plants of the new cultivar grown outdoors in a full sun display garden with supplemental water and fertilizer as needed at a wholesale nursery in Zeeland, Michigan. No plant growth regulators have been used. Plants of the new cultivar have not been tested under all possible conditions. The phenotype may vary with changes in the environment, climate, and cultural conditions without a change in the genotype. The color reference is in accordance with the 2015 edition of The Royal Horticultural Society Colour Chart except where general color dictionary terms are used.

Botanical designation: *Delosperma* hybrid;

Cultivar denomination: 'Electric Slide';

Parentage: The female parent is 'PJS01S'; the male parent is 'John Proffitt';

Asexual propagation: Terminal vegetative cuttings;

Root description: Thin, fibrous, freely branching; light tan, color nearest RHS NN155B depending on soil matrix;

Habit: Low sprawling mound; freely-branching; winter-hardy perennial; to about 60 cm wide and 6 cm tall;

Foliage: Opposite; linear; sessile; succulent; sarcous; with acute apex; truncate partially clasping base; entire margins; slightly concavo-convex; adaxial and abaxial surface glandular and slightly lustrous; to about 25 mm long, 6 mm wide slightly distal to center and 3 mm thick;

Leaf color: Adaxial and abaxial young between RHS 138A and RHS 138B, adaxial and abaxial mature color between RHS 146D and RHS 145A in basal 3 to 4 mm, distally nearest RHS 137B;

Venation: Veins not distinguishable from leaf;

Stem: Stoloniferous; cylindrical; sarcous; slightly lustrous; glabrous; to about 10 cm long and 3 mm diameter; branching at nodes;

Nodes: Average about 3 mm diameter; internode distance about 12 mm apart, greater distances distally and shorter at stem base; node color same as surrounding stem;

Branches: To about 8 cm long and 2 mm diameter;

Stem and branch color: Proximally nearest RHS 165D, top exposed portion between RHS 177D and RHS 146B, bottom shaded portion between RHS 145B and RHS 145C;

Petiole: Sessile;

Inflorescence: Single; radial; complete; perfect; actinomorphic;

Flower bud: Ellipsoidal; upright; to about 21 mm tall, 5 mm diameter at apex, and 10 mm diameter at calyx; exposed petal color nearest RHS 72A in petal center and nearest RHS 61A on petal margin; sepals nearest RHS 138A;

Bloom period: With strong flower coverage beginning late May for about 6 weeks and continuing again sporadically until hard frost in Zeeland, Michigan;

Inflorescence lasting: Two to three days in fully open state; upwardly;

Individual flower size: To about 32 mm across, 10 mm deep;

Petals: To about 30 per flower; linear to spatulate; apex emarginate with one to two notches to about 0.5 mm deep; base truncate; margin entire; strongly lustrous adaxial and abaxial; slightly arcuate downwardly; to about 20 mm long, 3 mm across toward apex, and 1 mm across at base;

Petal color: When first open adaxial and abaxial between RHS NN78A and RHS N78A with the proximal one-third adaxial nearest RHS NN78A; when mature adaxial nearest NN78A and abaxial nearest RHS N78A;

Petaloid: About 30 to 38; linear; narrowly acute apex; truncate base; entire margin; to about 4 mm long and 0.5 mm across, decreasing toward center;

Petaloid color: Adaxial and abaxial nearest RHS 70D;

Flower fragrance: Not observed in the present growing conditions;

Sepal: Five; in a single whorl; ovate to narrowly deltoid; with acute apex and truncate base; margin entire; adaxial and abaxial glabrous, glandular; succulent; size variable, about 10 mm long and 4 mm to 5 mm wide at fusion, fused in basal 5 mm into hypanthium;

Sepal color: Variable; adaxial and abaxial nearest RHS NN137B and a blend between RHS 147B and RHS N187A toward apex and margin and proximal base nearest RHS 138B;

Pedicel: Cylindrical; glandular; succulent; to about 50 mm long and 3 mm diameter;

Pedicel color: Between RHS 146D and RHS 145B;

Gynoecium: Penta-merous; to about 6 mm long;

Pistil: Five; highly reduced, stigma and style indistinguishable; with stigmatic papillae; conic; to about 3 mm long and 1.5 mm across; color nearest RHS 163C;

Androecium: Quantity about 55 to 60;

*Filament.*—55 to 60; cylindrical; mostly straight; glabrous; lustrous; to 3 mm long and 0.3 mm diameter; color nearest RHS N155B.

*Anther.*—Elliptical; to about 1 mm long and 0.5 mm across; color nearest RHS 11B.

*Pollen.*—Abundant; color nearest RHS 10A.

Fruit: Penta-dehiscent capsule; to about 9 mm across and 8 mm tall; color nearest RHS 161C at maturity;

Seed: To about 50 to 60 per flower; ellipsoidal; glabrous; about 0.5 mm long and 0.3 mm across; color variable, nearest RHS N199C, and between RHS 164D and RHS 164C;

Disease resistance: The new plant has not been observed to demonstrate either resistance or susceptibility to diseases and pests which might commonly be found on *Delosperma.*

Growth: The new plant has been shown to be hardy to at least USDA Zones 6 through 9 and tolerant of drought and high heat conditions.

I claim:

1. A new and distinct cultivar of *Delosperma* plant named 'Electric Slide' as herein illustrated and described.

* * * * *